(12) United States Patent
Poppi et al.

(10) Patent No.: US 7,145,158 B2
(45) Date of Patent: Dec. 5, 2006

(54) DEVICE FOR TREATING A PACKAGING MATERIAL BY MEANS OF UV RADIATION

(75) Inventors: Luca Poppi, Modena (IT); Guido Moruzzi, Bologna (IT); Paolo Benedetti, Modena (IT)

(73) Assignee: Tetra Laval Holding & Finance S.A., Pully (CH)

( * ) Notice: Subject to any disclaimer, the term of this patent is extended or adjusted under 35 U.S.C. 154(b) by 238 days.

(21) Appl. No.: 10/502,398

(22) PCT Filed: Mar. 11, 2003

(86) PCT No.: PCT/EP03/02471

§ 371 (c)(1),
(2), (4) Date: Jul. 26, 2004

(87) PCT Pub. No.: WO03/076273

PCT Pub. Date: Sep. 18, 2003

(65) Prior Publication Data

US 2005/0077482 A1    Apr. 14, 2005

(30) Foreign Application Priority Data

Mar. 12, 2002    (IT) .......................... TO2002A0215

(51) Int. Cl.
     *G21G 5/00*    (2006.01)
(52) U.S. Cl. ................ 250/504 R; 250/505.1
(58) Field of Classification Search ............ 250/504 R, 250/432 R, 433, 505.1, 515.1; 422/24, 26, 422/22; 313/486, 489
See application file for complete search history.

(56) References Cited

U.S. PATENT DOCUMENTS

| 3,904,361 A | 9/1975 | Egger |
| 3,994,686 A | 11/1976 | Rauser et al. |
| 4,005,135 A | 1/1977 | Helding |
| 4,037,112 A | 7/1977 | Ramler et al. |
| 4,056,921 A | 11/1977 | Gilliand et al. |
| 4,225,556 A | 9/1980 | Lothman et al. |
| 4,289,728 A | 9/1981 | Peel et al. |
| 4,305,000 A | 12/1981 | Cheever |
| 4,366,125 A | 12/1982 | Kodera et al. |
| 4,375,145 A | 3/1983 | Mosse et al. |
| 4,797,255 A | 1/1989 | Hatanaka et al. |
| 4,944,132 A | 7/1990 | Carlsson et al. |
| 4,992,247 A | 2/1991 | Foti |

(Continued)

FOREIGN PATENT DOCUMENTS

EP    361 858 A1    4/1990

(Continued)

OTHER PUBLICATIONS

Rutherford et al., "Method to sensitize bacterial spores to subsequent killing by dry heat or ultraviolet irradiation", Journal of Microbiological Methods, 2000, pp. 281-290, vol. 42, Elsevier Biomedical, Amsterdam, Holland.

(Continued)

*Primary Examiner*—Kiet T Nguyen
(74) *Attorney, Agent, or Firm*—Buchanan Ingersoll & Rooney PC

(57) ABSTRACT

A device (1) for treating a packaging material (2) by means of UV radiation, the device having a source (6) of such radiation, and a protective screen (8) interposed between the source (6) and the material (2) for treatment; the screen (8) has a film (9) of a polymer resistant and permeable to UV radiation, and which is flexible, does not tear, and does not form fragments.

15 Claims, 1 Drawing Sheet

U.S. PATENT DOCUMENTS

| | | | |
|---|---|---|---|
| 5,069,017 A | 12/1991 | Fabricius | |
| 5,114,670 A | 5/1992 | Duffey | |
| 5,124,212 A | 6/1992 | Lee et al. | |
| 5,129,212 A | 7/1992 | Duffey et al. | |
| 5,178,841 A | 1/1993 | Vokins et al. | |
| 5,213,759 A | 5/1993 | Castberg et al. | |
| 5,326,542 A | 7/1994 | Sizer et al. | |
| 5,364,645 A | 11/1994 | Lagunas-Solar et al. | |
| 5,368,828 A | 11/1994 | Carlson | |
| 5,433,920 A | 7/1995 | Sizer et al. | |
| 5,446,289 A | 8/1995 | Shodeen et al. | |
| 5,451,367 A | 9/1995 | Stack et al. | |
| 5,547,635 A | 8/1996 | Duthie, Jr. | |
| 6,145,276 A | 11/2000 | Palm et al. | |
| 6,202,384 B1 | 3/2001 | Kurth et al. | |
| 6,614,039 B1 * | 9/2003 | Hollander | 250/504 R |

FOREIGN PATENT DOCUMENTS

| | | |
|---|---|---|
| EP | 0 424 153 B1 | 4/1991 |
| EP | 0 580 176 A1 | 1/1994 |
| EP | 1 074 186 A3 | 2/2001 |
| EP | 0 919 246 B1 | 4/2002 |
| JP | 62-4038 | 1/1987 |
| JP | 02-4621 | 1/1990 |
| WO | WO 97/35768 | 10/1997 |

OTHER PUBLICATIONS

Reidmiller et al., "Characterization of UV-Peroxide Killing of Bacterial Spores", Journal of Food Protection, 2003, pp. 1233-1240, vol. 66, No. 7, New York, New York.

Bagyan et al., "The katX Gene, Which Codes for the Catalase in Spores of *Bacillus subtilis*, Is a Forespore-Specific Gene Controlled by $\sigma^{oF}$, and KatX Is Essential for Hydrogen Peroxide Resistance of the Germinating Spore", Journal of Bacteriology, 1998, pp. 2057-2062, vol. 180, No. 8, American Society for Microbiology, Washington, D.C.

Bayliss, et al., "The Combined Effect of Hydrogen Peroxide and Ultraviolet Irradiation on Bacterial Spores", Journal of Applied Bacteriology, 1979, pp. 263-269, vol. 47, American Society for Microbiology, Washington, D.C.

Bayliss et al., "The synergistic killing of spores of *Bacillus subtilis* by Hydrogen Peroxide and UltraVioliet Light Irradiation," FEMS Microbiology Letters, 1979, pp. 331-333, vol. 5, Elsevier Science Publishers, Amsterdam, Holland & New York.

* cited by examiner

DEVICE FOR TREATING A PACKAGING MATERIAL BY MEANS OF UV RADIATION

TECHNICAL FIELD

The present invention relates to a device for treating a packaging material by means of UV radiation.

UV radiation has long been used in a wide range of applications. In the food industry, for example, it is commonly used for disinfecting or sterilizing packaging material, or for surface treating the food products themselves.

UV radiation is also used for disinfecting work environments.

The device according to the present invention may conveniently be used, though not exclusively, in a packaging material sterilizing unit of a pourable food product packaging machine, to which application reference is made in the following description purely by way of a non-limiting example.

BACKGROUND ART

Various types of machines are known for packaging various types of pourable food products, such as fruit juice, wine, tomato sauce, pasteurized or long-storage (UHT) milk, etc.

Such machines have different characteristics, depending on the type of package used, e.g. packages made of strip or sheet material, cups, bottles, tubs, etc.

One of the best-known packaging machines is the one marketed under the registered trademark Tetra Brik®—referred to purely by way of a non-limiting example—in which the packages or packs are formed from a continuous tube of packaging material defined by a longitudinally sealed web.

The packaging material has a multilayer structure comprising a layer of paper material covered on both sides with layers of heat-seal material, e.g. polyethylene. In the case of aseptic packages for long-storage products, such as UHT milk, the packaging material comprises a layer of barrier material, e.g. aluminium foil, which is superimposed on a layer of heat-seal plastic material, and is in turn covered with another layer of heat-seal plastic material eventually defining the inner face of the package and therefore contacting the food product.

To produce aseptic packages, the web of packaging material is unwound off a reel and fed through a sterilizing unit, in which it is sterilized, for example, by immersion in a bath of liquid sterilizing agent, such as a concentrated solution of hydrogen peroxide and water.

Alternatively, or in addition to being treated with a liquid sterilizing agent, the web of packaging material may be treated by exposure to one or more sources of UV electromagnetic radiation, as described, for example, in European Patent Application EP-A-919246.

Downstream from the sterilizing unit, the web of packaging material is maintained in an aseptic chamber, in which it is dried, folded into a cylinder, and sealed longitudinally to form a continuous vertical tube. In other words, the tube of packaging material forms an extension of the aseptic chamber, is filled continuously with the pourable food product, and is then fed to a forming and (transverse) sealing unit for producing the individual packages, and in which the tube is gripped between pairs of jaws and sealed transversely to form aseptic pillow packs.

The pillow packs are separated by cutting the sealed portions in between, and are then fed to a final folding station where they are folded mechanically into the finished form.

Packaging machines of the type described above are used widely and satisfactorily in a wide range of food industries for producing aseptic packages from strip packaging material. Performance of the sterilizing unit, in particular, amply ensures conformance with regulations governing the sterility of the packages.

Within the industry, however, a demand exists for further improvement, particularly as regards the safety of UV devices, which may be used for both disinfecting and sterilizing various types of packaging material, such as strip and sheet material, cups, bottles, tubs, etc.

UV devices substantially comprise a UV radiation source housed in a casing and protected at the front by a screen made of material resistant and permeable to UV radiation. In commonly marketed devices, the screen is defined by a quartz plate.

Though perfectly suitable in terms of physical-chemical properties, quartz has various drawbacks. In particular, it is extremely expensive. Moreover, a quartz screen is fragile and, if broken, tends to form extremely hard, sharp fragments. In known machines, the UV device, and therefore the quartz screen, is so located as to be protected against impact, so that the risk of it breaking and leaving trace fragments of quartz on the packaging material is highly unlikely. Nevertheless, at present, the possibility cannot be entirely excluded. Though unlikely, breakage may be caused by anomalous vibration or thermal stress, by flaws in the structure of the material, by accidental forcing or impact during assembly, or by a combination of any of these.

Another drawback of quartz in this type of application is its tendency to dirty easily in normal operating conditions, and where it is extremely difficult, expensive, or even impossible to clean, whereas replacement is far from cheap.

Quartz also has the further drawback of any flaws, cracks, dirt, etc. locally affecting its optical properties, thus possibly resulting in uneven irradiation of the material being treated.

DISCLOSURE OF INVENTION

It is an object of the present invention to provide a device for UV irradiation treatment of a packaging material, designed to eliminate the aforementioned hazards typically associated with known devices.

According to the present invention, there is provided a device for treating a packaging material by means of UV radiation, the device comprising a source of said radiation, and a screen for protecting said source and which is interposed between the source and the material for treatment; characterized in that said screen comprises a film of a polymer resistant and permeable to said UV radiation.

Using a film of a polymer resistant and permeable to UV radiation provides for meeting the requirements of chemical/physical compatibility with the workplace, and at the same time for eliminating the drawbacks typically associated with quartz plates.

In particular, the flexibility of the polymer material substantially eliminates any risk of tearing caused by vibration or thermal stress. And, even in the highly unlikely event of the film tearing, no fragments are formed, thus making the material perfectly suitable for use in the food industry.

Moreover, a film of polymer material is much cheaper than a quartz plate, and can therefore be replaced quickly and cheaply in the event of soiling.

Finally, in the event of flaws in the structure, i.e. on the surface, of the polymer film, uniform irradiation of the material being treated is unaffected, the polymer film being by nature slightly translucent and therefore still capable of ensuring adequate UV radiation diffusion.

In a preferred embodiment of the present invention, the polymer is fluorinated or, better still, completely fluorinated and in the perfluoroalkoxy (PFA) class.

More preferably, the fluorinated polymer is an MFA, the characteristics of which are particularly favourable in terms of UV radiation transmission, even, for example, in the case of UV radiation with a 222 nm wavelength, as described in the aforementioned European Patent Application EP-A-919246.

In one possible embodiment of the invention, the polymer film is supported between substantially rigid grilles.

BRIEF DESCRIPTION OF THE DRAWINGS

A preferred, non-limiting embodiment of the present invention will be described by way of example with reference to the accompanying drawings, in which.

BEST MODE FOR CARRYING OUT THE INVENTION

Figure 1:
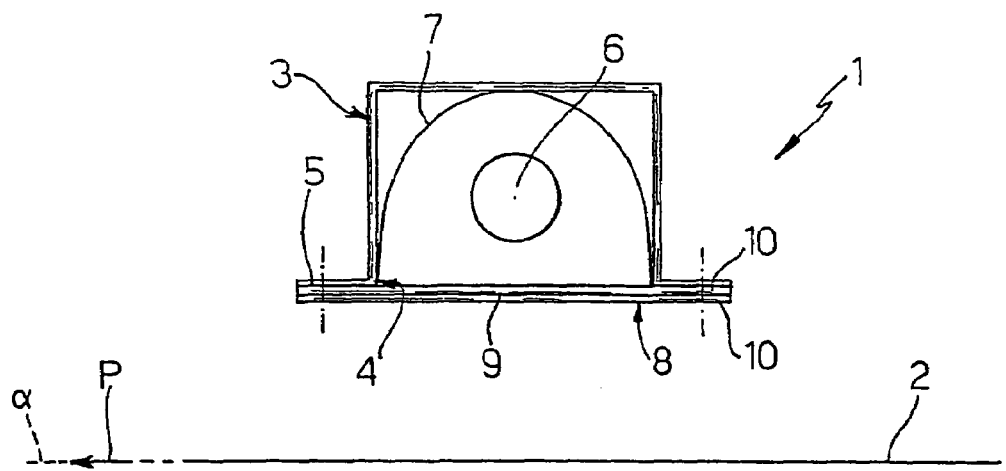
FIG. 1 shows a section of a device for treating packaging material in accordance with the invention.
Figure 2:
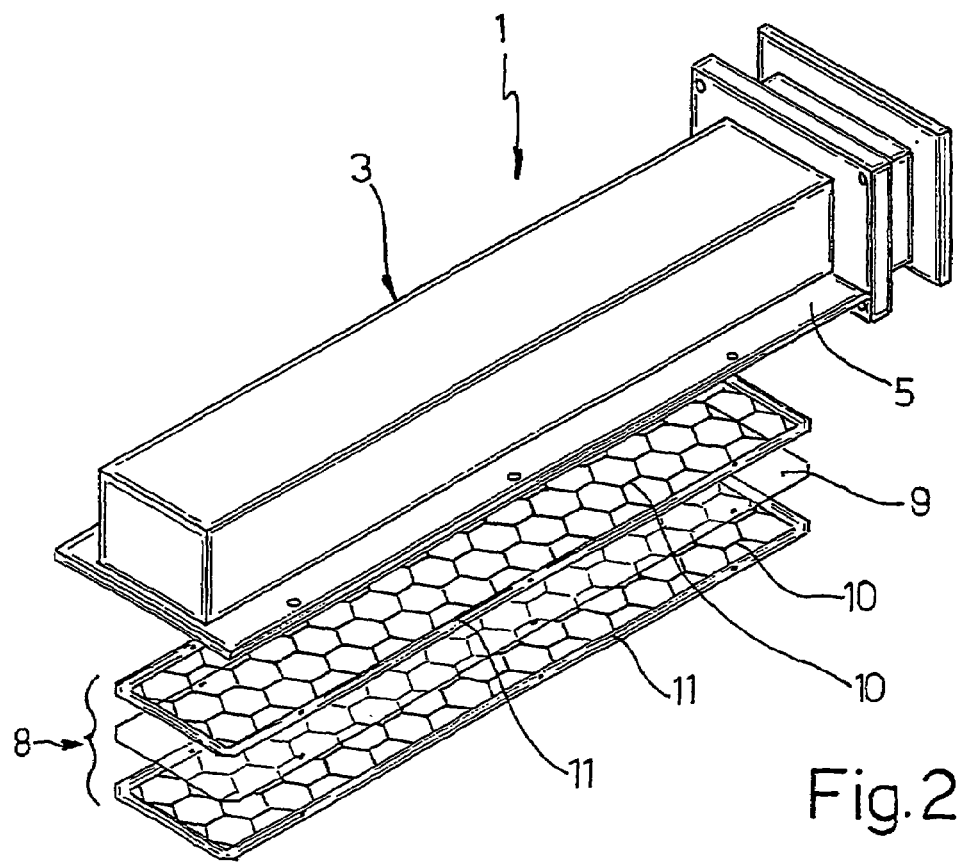
FIG. 2 shows a partly exploded view in perspective of the FIG. 1 device.

Number 1 in the accompanying drawings indicates as a whole a device for treating a packaging material 2 for producing packages of a pourable food product.

By way of a non-limiting example, the packaging material is a sheet material.

Material 2 is fed continuously in known manner along a path P in a plane a of the material.

Material 2 may be defined by a different type of material, such as a tub, cup, bottle, etc.

Device 1 extends crosswise to material 2, i.e. perpendicularly to path P and parallel to plane α, and comprises an elongated outer casing 3 open on the side facing material 2 so as to form a window 4 defined by a peripheral flange 5. Device 1 also comprises a UV radiation source 6 housed longitudinally in casing 3, which is provided in conventional manner with a lining 7 of reflecting material.

Source 6 emits UV radiation of a wavelength, for example, of 222 nm.

The device also comprises a protective screen 8 fixed at the front to flange 5 so as to close window 4.

According to the present invention, screen 8 comprises a film 9 of a polymer material resistant and permeable to the UV radiation emitted by source 6.

The polymer material may be of any type, providing it is transparent to UV radiation (T≧80%) and resistant to said UV radiation in the operating conditions and for the time period between two successive replacements.

The polymer material may, for example, be in the polyolefin group, such as PE or PP.

Depending on the different resistance to UV radiation of different possible types of polymer film, provision may be made for appropriate, programmed, periodic replacement of film 9 of polymer material, so as to ensure constant mechanical and optical properties of the film.

Replacement may be made, for example, either at given times, or continuously, using a strip of polymer material moving continuously between two appropriately powered reels.

In a preferred embodiment, the material is a fluorinated polymer, or a completely fluorinated polymer in the perfluoroalkoxy (PFA) class, and even more preferably is an MFA, e.g. the MFA produced by AUSIMONT® under the trade name HYFLON® MFA.

Film 9 is conveniently 20 to 200 μm thick, is preferably 40 μm, 50 μm, or 100 μm thick, and is in the form of a flexible, slightly translucent film capable of diffuse transmission of a fraction of the incident radiation.

Though film 9, by virtue of its physical characteristics, may be used alone and simply fixed along the edges to flange 5, it is preferably interposed between two substantially rigid metal supporting grilles 10, which are fixed to flange 5 by means of respective peripheral frames 11, and provide for protecting and keeping the film flat.

Film 9 has excellent characteristics in terms of transmittance and resistance to ageing under UV radiation, as shown in the following examples.

EXAMPLE 1

A 50 μm thick film of Hyflon® MFA was exposed to 300 KJ/cm2 UV radiation of 222 nm wavelength for 800 hours. After exposure, the film showed no visible alteration, and 90% transmittance referred to the above 222 nm wavelength.

EXAMPLE 2

A 100 μm thick film of Hyflon® MFA was exposed to 300 KJ/cm2 UV radiation of 222 nm wavelength for 800 hours. After exposure, the film showed no visible alteration, and 82% transmittance referred to the above 222 nm wavelength.

Film 9 does not tear in the event of anomalous thermal stress or vibration, and, even if torn by accidental impact, which is substantially impossible in working conditions, does not produce fragments.

Film 9 is also much cheaper than a conventional quartz plate.

Clearly, changes may be made to the present invention without, however, departing from scope of the invention itself.

In particular, the screen may be made of a different polymer material, e.g. PE, PP, PFA or many others.

Also, grilles 10 may be different or even dispensed with.

The invention claimed is:

1. A device for treating a packaging material by UV radiation, the device comprising a source of said radiation, and a screen for protecting said source and which is interposed between the source and the material for treatment; wherein said screen comprises a film of a polymer resistant and permeable to said UV radiation, and a pair of substantially rigid grilles between which said film is supported.

2. A device as claimed in claim 1, wherein said polymer is fluorinated.

3. A device as claimed in claim 2, wherein said film is of a thickness ranging between 20 and 200 μm.

4. A device as claimed in claim 3, wherein the thickness of said film is selected between 40 μm or 100 μm.

5. A device as claimed in claim 1, wherein said polymer is completely fluorinated.

6. A device as claimed in claim 5, wherein said polymer is in the perfluoroalkoxy (PFA) class.

7. A device as claimed in claim 6, wherein said film is of a thickness ranging between 20 and 200 μm.

8. A device as claimed in claim 7, wherein the thickness of said film is selected between 40 μm or 100 μm.

9. A device as claimed in claim 5, wherein said film is a of a thickness ranging between 20 and 200 μm.

10. A device as claimed in claim 9, wherein thickness of said film is selected between 40 μm or 100 μm.

11. A device as claimed in claim 1, wherein said polymer is an MFA.

12. A device as claimed in claim 11, wherein film is of a thickness ranging between 20 and 200 μm.

13. A device as claimed in claim 12, wherein the thickness of said film is selected between 40 μm or 100 μm.

14. A device as claimed in claim 1, wherein said film is of a thickness ranging between 20 and 200 μm.

15. A device as claimed in claim 14, wherein the thickness of said film is selected between 40 μm or 100 μm.

* * * * *